United States Patent
Markert et al.

(12)

(10) Patent No.: US 6,297,390 B1
(45) Date of Patent: Oct. 2, 2001

(54) METHOD FOR PREPARING OPTICALLY ACTIVE 5-METHYL-2-(1-METHYL-BUTYL)-5-PROPYL-1,3-DIOXAN

(75) Inventors: Thomas Markert, Monheim; Dirk Merkel, Solingen; Hans-Josef Altenbach, Wuppertal, all of (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/462,706

(22) PCT Filed: Jul. 3, 1998

(86) PCT No.: PCT/EP98/04107

§ 371 Date: Apr. 3, 2000

§ 102(e) Date: Apr. 3, 2000

(87) PCT Pub. No.: WO99/02515

PCT Pub. Date: Jan. 21, 1999

(30) Foreign Application Priority Data

Jul. 11, 1997 (DE) ............................................. 197 29 840

(51) Int. Cl.⁷ ........................ C07D 319/06; C07D 319/12
(52) U.S. Cl. ............................................. 549/369; 549/376
(58) Field of Search ...................................... 549/369, 376

(56) References Cited

U.S. PATENT DOCUMENTS 4,372,880  2/1983  Upadek et al. .................. 252/522 R

FOREIGN PATENT DOCUMENTS 30 16 007  11/1981  (DE) .

*Primary Examiner*—Amelia Owens
(74) *Attorney, Agent, or Firm*—John E. Drach; Steven J. Trzaska

(57) ABSTRACT

The present invention relates to a method for preparing optically active 5-methtyl-2-(1-methtyl-butyl)-5-propyl-1,3-dioxan, wherein said method comprises the following steps: converting lactic acid methylic ester into the corresponding N,N-disubstituted amid (aminolysis with piperidine and/or pyrrolidine); protecting its free OH function by a reaction with ethylvinylether in the presence of p-pyridiniumtosylate as a catalyst; submitting the N-pentamethylen- or N-tetramethylenlactamide thus obtained to a Grignard reaction in a conventional way so as to produce the corresponding α, β-unsaturated ketone; further separating in a conventional way (e.g. agitation with acetic acid) the protection group introduced during the second step; acetalating in a conventional way the ketone function (e.g. by reaction with 2-methyl-2-propyl-1,3-propanediol); mesylating the free OH function by reaction with methansulfonic acid chloride in pyridine; submitting the intermediate thus obtained to a reducing 1,2-transposition in the presence of trimethylammonium and diisobutylaluminum hydride while maintaining the sterochemistry; and converting by catalytic hydrogenation the dehydro compound thus abtained into optically active 5-methyl-2-(1-methyl-butyl)-5-propyl-1,3-dioxan. The optically active 5-methyl-2-(1-methyl-butyl)-5-propyl-1,3-dioxan of the present invention exhibits a remarkable scent profile as well as a high scent intensity and may be used as perfume.

2 Claims, No Drawings

METHOD FOR PREPARING OPTICALLY ACTIVE 5-METHYL-2-(1-METHYL-BUTYL)-5-PROPYL-1,3-DIOXAN

BACKGROUND OF THE INVENTION

1. Field of the Invention

This invention relates to a process for the production of optically active 5-methyl-2-(1-methylbutyl)5-propyl-1,3-dioxane, to the product obtainable by this process and to its use as a perfume.

2. Statement of Related Art

Judging by demand, many natural perfumes are available in totally inadequate quantities. For example 5000 kg of rose blossoms are required to produce 1 kg of rose oil. The consequences are extremely limited annual world production and a high price. Accordingly, it is clear that there is a constant need in the perfume industry for new perfumes with interesting fragrance notes in order to extend the range of naturally available perfumes, to make the necessary adaptations to changing fashion trends and to be able to meet the steady increasing demand for odor enhancers for products of everyday use, such as cosmetics and cleaners.

Accordingly, it is dear that there is a constant need in the perfume industry for new perfumes with interesting fragrance notes in order to extend the range of naturally available perfumes, to make the necessary adaptations to changing fashion trends and to be able to meet the steadily increasing demand for odor enhancers for products of everyday use, such as cosmetics and cleaners.

In addition, there is generally a constant need for synthetic perfumes which can be favorably produced in a consistent quality and which have desirable olfactory properties, i.e. pleasant, near-natural and qualitatively new odor profiles of adequate intensity, and which are capable of advantageously influencing the fragrance of cosmetic and consumer products. In other words, there is a constant need for compounds which have characteristic new odor profiles coupled with high staying power, intensity of odor and emanative power. 5-Methyl-2-(1-methylbutyl)-5-propyl-1,3dioxane 22 (trade name Troënan®)

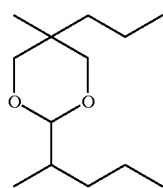

22 is a known synthetic perfume obtainable from 2-methyl pentanal 23 (cf. following scheme). The educt 23 is reacted with 2 equivalents of formaldehyde in a crossed Canizzaro reaction to form 2-methyl-2-propylpropane-1,3-diol 24. The diol 24 may then be acetalized with 2-methylpentanal 23 to form Troënan® 22.

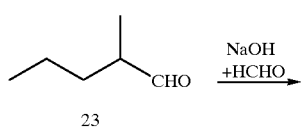

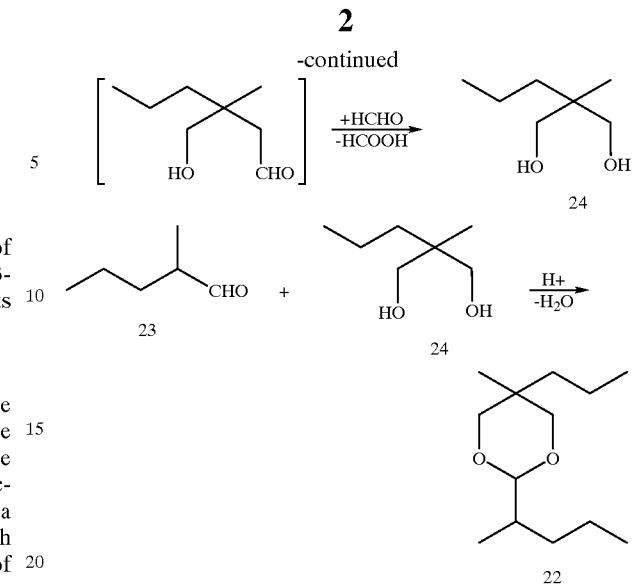

By virtue of its privet blossom note, Troënan® is valued for flowery and aromatic formulations, more particularly lily-of-the-valley compositions. It has the advantage over other lily-of-the-valley components that it is stable to alkalis.

Troënan® 22 contains two cis/trans isomers which in turn consist of two enantiomers:

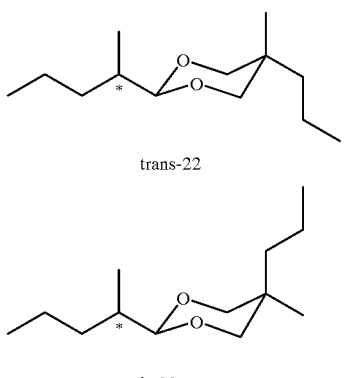

trans-22 cis-22

DESCRIPTION OF THE INVENTION

In exploratory investigations conducted by applicants using the technique of "GC Sniffing", it was surprisingly found that the trans isomer of Troënan® has the typical privet note while the cis isomer has a weak flowery-bergamotish note.

The problem addressed by the present invention was to provide a 5-methyl-2-(1-methylbutyl)-5-propyl-1,3-dioxane with a more attractive odor than the known commercial product Troënan®.

The problem stated above has been solved by an optically active 5-methyl-2-(1-methylbutyl)-5-propyl-1,3-dioxane which was obtained by multistage chiral pool synthesis from enantiomeric (S)-(−)-lactic acid methyl ester 56.

The synthesis according to the invention starts our from commercially obtainable enantiomeric (S)-(−)-lactic acid methyl ester 56 which, in a first step, is reacted to form an N,N-disubstituted amide. After protection of the OH function, the amide group is converted by a Grignard reaction into an α,β-unsaturated ketone 56. After removal of the protective group and subsequent acetalization, the hydroxy group is converted into the mesylate 57. After the reductive 1,2-rearrangement with the stereo-chemistry intact, a "dehydro-Troënan" 58 is converted by catalytic hydrogenation into the optically active 5-methyl-2-(1-methylbutyl)-5propyl-1,3-dioxane (−)-22.

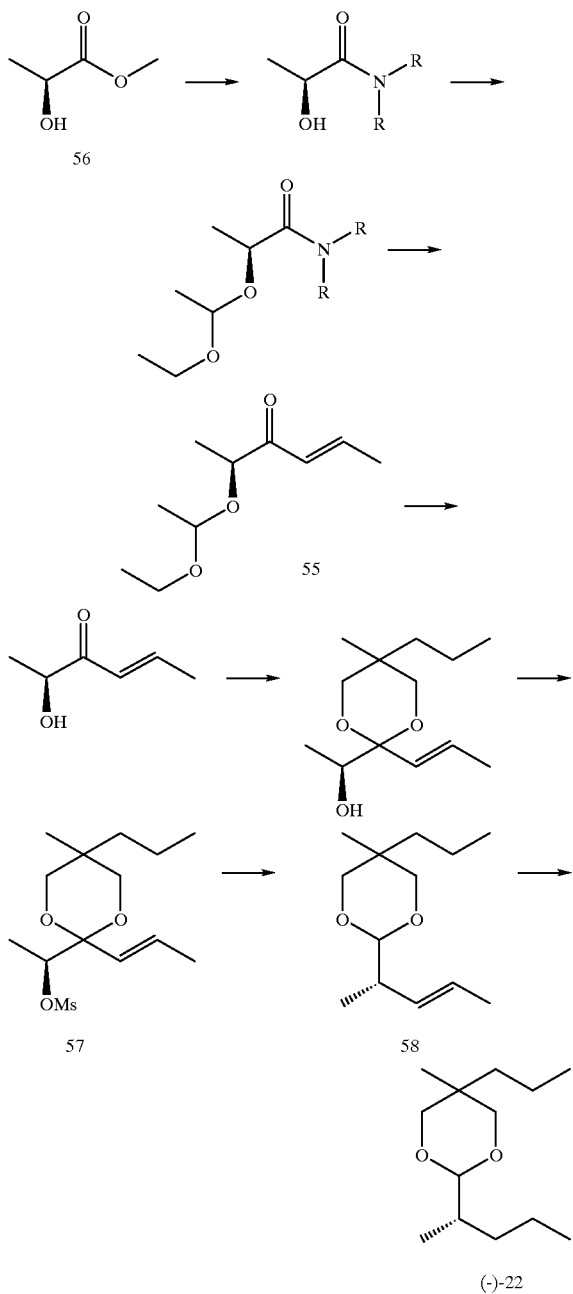

The $^1$H-NMR spectrum of (−)-22 agrees with that of the cis/trans mixture of Troënan® 22.

Determination of the angle of rotation produced a specific rotation angle $[\alpha]^{20}_D = -2.43°$.

An optically active (−)-22 was obtained as a cisatrans mixture by the chiral pool synthesis. It was found that this (−)-22 was surprisingly superior in its olfactory properties to commercially available Troënan® both from the qualitative point of view (typical odor profile) and from the odor intensity point of view (quantitative aspect).

Accordingly, the present invention relates to a process for the production of optically active 5-methyl-2-(1-methylbutyl)-5-propyl-1,3-dioxane by converting lactic methyl ester into the corresponding N,N-disubstituted amide (aminolysis with piperidine and/or pyrrolidine), protecting its free OH function by reaction with ethyl vinyl ether in the presence of p-pyridinium tosylate, subjecting the N-pentamethylene or N-tetramethylene lactamide thus obtained to a Grignard reaction in known manner to form the corresponding α,β-unsaturated ketone, removing the protective group introduced in the second stage in known manner (for example by stirring with acetic acid), acetalizing the ketone function in known manner (for example by reaction with 2-methyl-2-propylpropane-1,3-diol), mesylating the free OH function by reaction with methane sulfonic acid chloride in pyridine, subjecting the intermediate product thus obtained to a reductive 1,2-rearrangement in the presence of diisobutyl aluminum hydride and triethyl aluminum with the stereochemistry intact and converting the dehydro compound thus obtained into the optically active 5-methyl-2-(1-methylbutyl)-5-propyl-1,3-dioxane by catalytic hydrogenation.

The optically active 5-methyl-2-(1-methylbutyl)-5-propyl-1,3-dioxane obtainable by the process according to the invention has a surprisingly strong emanative power and captivates by its intensive privet and muguet note.

The present invention also relates to optically active 5-methyl-2-(1-methylbutyl)-5-propyl-1,3-dioxane obtainable by the process according to the invention.

The present invention also relates to the use of the optically active 5-methyl-2-(1-methylbutyl)-5-propyl-1,3dioxane obtainable by the process according to the invention as a perfume.

The following Examples are intended to illustrate the invention without limiting it in any way.

EXAMPLES 1.1 General observations

The following instruments and materials were used:
Melting points:
The melting points mentioned were determined with a melting point microscope (Reichert Thermovar) and are not corrected.
Rotation angles:
The rotation angles were measured with a Perkin-Elmer 241 polarimeter. The concentration c shown in connection with the specific rotation angle is defined as the quantity of substance (in g) per 100 ml of solution.
IR spectroscopy:
The IR spectra were recorded with a Perkin-Elmer 983 spectrometer.
The intensities of the absorption bands mentioned are described by the symbols s (strong), m (medium) and w (weak).
NMR spectroscopy:
The NMR spectra were recorded with Bruker ARX 400, AMX 400 and AC 200 F spectrometers. The chemical shifts are shown in δ-values, based on the standard. In the case of the ARX 400 spectrometer, the solvent used was employed as the standard; in the case of the AMX 400 and AC 200 F spectrometers, TMS was used as the internal standard.

The signal multiplicities are characterized by the symbols s (singlet), d (doublet), t (triplet), Ψ-t (pseudotriplet), q (quartet) and m (multiplet). To enable the hydrogen and carbon atoms to be unequivocally assigned, 2-D-COSY spectra ($^1H/^1H$ and $^1H/^{13}C$) and DEPT spectra were recorded.

The individual atoms were numbered in the same way in order to illustrate structural similarities and variations even in the spectrum. Accordingly, they do not always correspond to IUPAC rules.

In the case of compounds present in the form of cistrans mixtures, the signals were characterized by c for cis and t for trans where assignment was possible.

Mass spectroscopy:

The mass spectra were recorded with a Varian MAT 311 A.

Elemental analysis:

The elemental analysis was carried out with a Perkin-Elmer 240B microelemental analyzer.

Chromatographic processes:

The gas-chromatographic reaction control was carried out with a Hewlett-Packard GC 5710 A in conjunction with a DB-5 capillary column (I=30 m).

The chiral GC column investigations were carried out using a Shimadzu GC 14A in conjunction with a Cyclodex-beta-I/P capillary column (I=25 m).

The chiral HPLC column measurements were carried out with a Merck L7100/L7400 in conjunction with an OD-R column (I=250 mm, d=4 mm). A mixture of acetonitrile and water (50:50) was used as the mobile solvent (flow=0.8 ml/min.). Detection was carried out with a UV detector at 254 nm.

1.2 General procedures

The syntheses described in 1.3 were carried out inter alia by the following general procedures (AAV 1 to AAV 3). These procedures are as follows:

AAV 1: acetalization

1 Equivalent of the aldehyde and 1 equivalent of the diol are dissolved in cyclohexane with 0.025 equivalent of p-toluene sulfonic acid hydrate and the resulting solution is heated under reflux in a Dean-Stark apparatus (water separator), the water formed separating off. On completion of the reaction, the cooled solution is extracted by shaking with saturated sodium hydrogen carbonate solution until the washing water is no longer alkaline. The solution is dried over sodium sulfate and the solvent is removed under reduced pressure in a rotary evaporator. The residue is fractionated in an oil pump vacuum.

AAV 2: mesylation

1 Equivalent of the alcohol is dissolved in n ml of pyridine and the resulting solution is cooled to 0° C. 1.1 Equivalents of methane sulfonic acid chloride are added dropwise and the mixture is left in a refrigerator for 24 h at 4° C. It is then poured onto 2 n ml of ice and neutralized with semiconcentrated hydrochloric acid. The solution is extracted with ethyl acetate. After washing with saturated sodium hydrogen carbonate solution and drying over sodium sulfate, the solvent is removed in a rotary evaporator.

AAV 3: aminolysis

1 Equivalent of (S)-(−)-methyl lactate 56 and 2 equivalents of the amine are heated to 105° C. in a distillation assembly. The methanol formed is distilled off via a 15 cm Vigreux column. On completion of the reaction, the excess amine is distilled off and the product is fractionated at 0.1 mbar in the same assembly.

1.3 Chiral pool synthesis 1.3.1 Synthesis of N-pentamethylene lactamide 59

47.6 g of (S)-(−)-methyl lactate 56 (0.46 mole) are reacted with 78.2 g of piperidine (0.92 mole) by AAV 3. A clear colorless liquid is obtained after distillation.

Yield: 73%
Bp.: 111° C./0.8 mbar
Rotation angle: $[\alpha]^{20}_D = -1.13°$ (c=12.7)

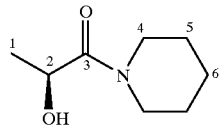

$^1$H-NMR (CDCl$_3$, 200 MHz): δ=4.4 (q, 1H; H-2), 3.6/3.35 (t, 4H, H-4 diastereotopic), 1.6 (m, 6H, H-5/H-6), 1.3 (d, 3H, H-1);

$^{13}$C-NMR (CDCl$_3$, 50 MHz): δ=173.9 (C-3), 64.0 (C-2), 45.8/43.5 (C-4), 26.2/25.5 (C-5), 24.4 (C-6), 21.4 (C-1);

MS (70 eV): m/z (%)=157 (18) [M$^+$], 114 (12) [C$_5$H$_8$O$_2$N$^+$], 113 (65) [C$_6$H$_{11}$ON$^+$], 112 (100) [C$_6$H$_{10}$ON$^+$], 85 (13) [C$_5$H$_{11}$N$^+$], 84 (15) [C$_5$H$_{10}$N$^+$], 69 (83) [C$_5$H$_9^+$], 56 (13) [C$_3$H$_6$N$^+$], 55 (12) [C$_3$H$_3$O$^+$], 45 (33) [C$_2$H$_5$O$^+$], 42 (18) [C$_2$H$_4$N$^+$], 41 (63) [C$_3$H$_5^+$]

| IR (Film): | ṽ [cm$^{-1}$] | vibration type |
|---|---|---|
| | 3415, s | O—H stretching vibration |
| | 2940, s | C—H stretching vibration |
| | 1635, s | C=O stretching vibration, amide |
| | 1480, s + 1400, s | C—H deformation vibration |
| | 1115, s | C—O stretching vibration |
| EA: | C$_8$H$_{15}$NO$_2$ | M = 157.21 g/mole |
| | calculated: | C = 61.12% H = 9.62% N = 8.91% |
| | observed: | C = 60.31% H = 9.63% N = 8.79% |

1.3.2 Synthesis of N-tetramethylene lactamide 60

31.2 g of (S)-(−)-methyl lactate 56 (0.3 mole) are reacted with 42.7 g of pyrrolidine (0.6 mole) by AAV 3. A clear colorless liquid is obtained after distillation.

Yield: 97%
Bp.: 95° C./0.1 mbar
Rotation angle: $[\alpha]^{20}_D = -48.67°$ (c=12.8)

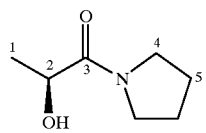

$^1$H-NMR (CDCl$_3$, 200 MHz): δ=4.35 (q, 1H; H-2), 3.65/3.3 (m, 4H, H-4 diastereotopic), 2.1–1.8 (m, 4H, H-5), 1.35 (d, 3H, H-1);

$^{13}$C-NMR (CDCl$_3$, 50 MHz): δ=173.5 (C-3), 65.6 (C-2), 46.2/46.0 (C-4), 26.1/23.9 (C-5), 20.6 (C-1);

MS (70 eV): m/z (%)=157 (18) [M$^+$], 114 (12) [C$_5$H$_8$O$_2$N$^+$], 113 (65) [C$_6$H$_{11}$ON$^+$], 112 (100) [C$_6$H$_{10}$ON$^+$], 85 (13)

[C₅H₁₁N⁺], 84 (15) [C₅H₁₀N⁺], 69 (83) [C₅H₉⁺], 56 (13) [C₃H₆N⁺], 55 (12) [C₃H₃O⁺], 45 (33) [C₂H₅O⁺], 42 (18) [C₂H₄N⁺], 41 (63) [C₃H₅⁺]

| IR (Film): | ṽ [cm⁻¹] | vibration type |
|---|---|---|
| | 3405, s | O—H stretching vibration |
| | 2975, s | C—H stretching vibration |
| | 1635, s | C=O stretching vibration, amide |
| | 1435, s + 1380, s | C—H deformation vibration |
| | 1128, s | C—O stretching vibration |
| EA: | C₇H₁₃NO₂ | M = 143.19 g/mole |
| | calculated: | C = 58.72% H = 9.15% N = 9.78% |
| | observed: | C = 58.29% H = 9.23% N = 9.58% |

1.3.3 Synthesis of the EE-protected N-pentamethylene lactamide 62

46.0 g of N-pentamethylene lactamide 59 (293 mmoles), 76.6 g of ethylvinyl ether and 7.53 g of p-pyridinium tosylate (30 mmoles) are dissolved in 200 ml of absolute dichloromethane. The solution is refluxed for 3 h. After cooling, the solution is washed with distilled water and saturated sodium hydrogen carbonate solution. The solvent is removed in a rotary evaporator and the residue is fractionated via a 15 cm Vigreux column. A clear colorless liquid is obtained.

Yield: 45% ; Bp.: 78° C./0.08 mbar; Rotation angle: $[\alpha]^{20}_D = -47.77°$ (c=17.6);

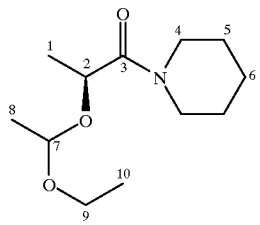

¹H-NMR (CDCl₃, 200 MHz): δ=4.80/4.70 (q, 1H; H-2), 4.6/4.5 (q, 1H, H-7), 3.55 (m, 6H, H-4/H-9), 1.65 (m, 6H, H-5/H-6), 1.45-1.30 (m, 6H, H-1/H-8), 1.2 (m, 3H, H-10); The protons at C² and C⁷ break up under the effect of the diastereomer mixture present.
¹³C-NMR (CDCl₃, 50 MHz): δ=170.8 (C-3), 99.3/98.9 (C-7), 70.4 (C-2), 61.3/60.3 (C-9), 46.1/43.2 (C4), 26.4/25.7 (C-5), 24.6 (C-6), 20.2 (C-8), 18.8/18.4 (C-1), 15.3 (C-10)

| IR (Film): | ṽ [cm⁻¹] | vibration type |
|---|---|---|
| | 2935, s | C—H stretching vibration |
| | 1640, s | C=O stretching vibration, amide |
| | 1440, s + 1375, m | C—H deformation vibration |
| | 1080, s | C—O stretching vibration |

1.3.4 Synthesis of the EE-protected N-tetramethylene lactamide 61

34.7 g of N-tetramethylene lactamide 60 (243 mmoles), 36.0 g of ethylvinyl ether (0.5 mmole) and 2.3 g of p-pyridinium tosylate (9 mmoles) are dissolved in 150 ml of absolute dichloromethane. The solution is stirred for 3 h at room temperature and then washed with distilled water and saturated sodium hydrogen carbonate solution. The solvent is removed in a rotary evaporator and the residue is fractionated via a 15 cm Vigreux column. A clear colorless liquid is obtained.

Yield: 76%

Bp.: 78° C./0.1 mbar

Rotation angle: $[\alpha]^{20}_D = -76.84°$ (c=10.2);

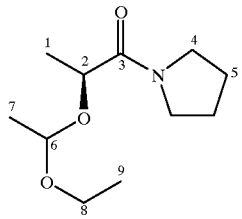

¹H-NMR (CDCl₃, 200 MHz): δ=4.80/4.75 (q, 1H; H-2), 4.5/4.35 (q, 1H, H-6), 3.7-3.3 (m, 6H, H-4/H-8), 2.05-1.75 (m, 4H, H-5), 1.4 (m, 6H, H-1/H-7), 1.15 (m, 3H, H-9);

The protons at C² and C⁶ break up under the effect of the diastereomer mixture present.

¹³C-NMR (CDCl₃, 50 MHz): δ=171.3 (C-3), 99.21/98.5 (C-6), 70.4/69.9 (C-2), 61.0/60.0 (C-8), 46.1 (C4), 26.4/23.8 (C-5), 20.0 (C-7), 18.2/17.9 (C-1), 15.4/15.2 (C-9)

| IR (Film): | ṽ [cm⁻¹] | vibration type |
|---|---|---|
| | 2980, s | C—H stretching vibration |
| | 1655, s | C=O stretching vibration, amide |
| | 1430, s + 1370, m | C—H deformation vibration |
| | 1085, s | C—O stretching vibration |

1.3.5 Synthesis of 2-hydroxyhex-4-en-3-one 63

3.6 g of magnesium turnings (150 mmoles) are introduced into 25 ml of THF, after which 18.2 g of 1-bromo-1-propene (150 mmoles) in 50 ml of THF are added dropwise over a period of 30 minutes. After stirring for 30 minutes at 35° C., 10.75 g of the EE-protected N-tetramethylene lactamide 61 (50 mmoles) in 25 ml of THF are added dropwise, followed by stirring for 3 h at 40° C. After the solution has been cooled, it is hydrolyzed with 2 n hydrochloric acid. The phases are separated and the aqueous phase is extracted with diethyl ether. The combined organic phases are neutralized with saturated sodium hydrogen carbonate solution. After the solvent has been removed in a rotary evaporator, part of the EE-protected 2-hydroxyhex-4-en-3-one 55 can be isolated from the residue. It is characterized as follows:

Bp.: 62° C./0.1 mbar

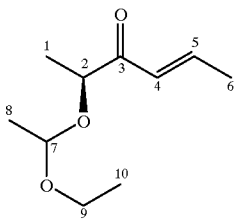

$^1$H-NMR (CDCl$_3$, 200 MHz): δ=7.0 (dq, 1H; H-5), 6.5 (Ψ-t, 1H, H-4), 4.75/4.65 (q, 1H, H-7), 4.35/4.2 (q, 1H, H-2), 3.65–3.35 (m, 2H, H-9), 1.95 (d, 3H, H-6), 1.35 (m, 6H, H-1/H-8), 1.15 (Ψ-q, 3H, H-10);
The protons at C$^2$ and C$^7$ break up under the effect of the diastereomer mixture present.
$^{13}$C-NMR (CDCl$_3$, 50 MHz): δ=200.5 (C-3), 144.5/143.5 (C-5), 126.6 (C-4), 99.8/99.5
(C-6), 76.1 (C-2), 61.7/60.7 (C-9), 20.1 (C-8), 18.4 (C-1), 16.1/15.3 (C-10)

| IR (Film): | ṽ [cm$^{-1}$] | vibration type |
|---|---|---|
| | 2980, s | C—H stretching vibration, aliphatic |
| | 1695, s | C=O stretching vibration, α,β-unsaturated ketone |
| | 1630, s | C=C stretching vibration, α,β-unsaturated ketone |
| | 1445, s + 1375, m | C—H deformation vibration |
| | 1080, s | C—O stretching vibration |

The protected compound 55 is refluxed for 30 minutes with 40 ml of 10% acetic acid. After cooling, the mixture is extracted with dichloro-methane. After drying over potassium carbonate, the solvent is removed and the residue is fractionated via a 15 cm Vigreux column. A clear light yellow liquid is obtained.

Yield: 54%
Bp.: 98° C./40 mbar
Rotation angle: $[α]^{20}_D$=−40.25° (c=3.5)

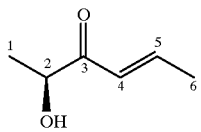

$^1$H-NMR (CDCl$_3$, 200 MHz): δ=7.05 (dq, 1H; H-5), 6.25 (d, 1H, H-4), 4.45 (q, 1H, H-2), 1.95 (d, 3H, H-6), 1.40 (d, 3H, H-1);
$^{13}$C-NMR (CDCl$_3$, 50 MHz): δ=201.1 (C-3), 145.5 (C-5), 126.4 (C4), 71.3 (C-2), 20.5 (C-6), 18.2 (C-1)

| IR (Film): | ṽ [cm$^{-1}$] | vibration type |
|---|---|---|
| | 3445, s | O—H stretching vibration |
| | 3025, w | C—H stretching vibration olefinic |
| | 2980, s | C—H stretching vibration, aliphatic |
| | 1690, s | C=O stretching vibration |
| | 1630, s | C=C stretching vibration α,β-unsaturated ketone |
| | 1440, s + 1375, s | C—H deformation vibration |
| | 1070, s | C—O stretching vibration |

1.3.6 Synthesis of 2-hydroxyethyl-5-methyl-2-(1-propenyl)-5-propyl-1,3-dioxane 64

2.9 g of 2-hydroxyhex-4-en-3-one 63 (25 mmoles) and 3.3 g of 2-methyl-2-propylpropane-1.3-diol 24 (25 mmoles) are acetalized in 50 ml of cyclohexane by AAV 1. After distillation through a spinning band column, a clear light yellow oil is obtained.

Yield: 40%;

Bp.: 73° C./0.1 mbar;

$^1$H-NMR (CDCl$_3$, 400.1 MHz): δ=5.85 (dq, 1H; H-5), 5.25 (d, 1H, H-4), 3.7–3.3 (m, 5H, H-2/H-7), 1.8 (d, 3H, H-6), 1.3 (m, 2H, H-9), 1.20/0.60 (s, 3H, H-12), 1.15 (d, 3H, H-8), 1.0 (q, 2H, H-10), 0.9 (t, 3H, H-11);
$^{13}$C-NMR (CDCl$_3$, 100.1 MHz): δ=132.5 (C-5), 127.2 (C-4), 100.5 (C-1), 73.3 (C-7), 70.9/69.9 (C-2), 38.9/36.7 (C-9), 32.7 (C-3), 20.1/19.4 (C-12), 17.8 (C-6), 16.8 (C-10), 16.1 (C-8), 14.7 (C-11)

MS (70 eV): m/z (%)=228 (1) [M$^+$], 183 (65) [M$^+$—C$_2$H$_5$O$^+$], 97 (22) [C$_6$H$_9$O$^+$], 69 (100) [C$_4$H$_5$O$^+$], 56 (14) [C$_4$H$_8^+$], 55 (68) [C$_3$H$_3$O$^+$], 45 (11) [C$_2$H$_5$O$^+$], 43 (33) [C$_3$H$_7^+$], 41 (27) [C$_3$H$_5^+$]

| IR (Film): | ṽ [cm$^{-1}$] | vibration type |
|---|---|---|
| | 3495, s | O—H stretching vibration |
| | 3020, w | C—H stretching vibration, olefinic |
| | 2960, s | C—H stretching vibration, aliphatic |
| | 1670, w | C=C stretching vibration |
| | 1470, m + 1390, m | C—H deformation vibration |
| | 1120, s | C—O stretching vibration |

1.3.7 Mesylation of 2-hydroxyethyl-5-methyl-2-(1-propenyl)-5-propyl-1,3-dioxane 64

12.6 g of 2-hydroxyethyl-5-methyl-2-(1-propenyl)-5-propyl-1,3-dioxane 64 (55 mmoles) are mesylated with 7.0 g of methane sulfonic acid chloride (61 mmoles) in 80 ml of pyridine by AAV 2. A clear light brown oil is obtained.

Yield: 92%;
Bp.: decomposition at T>105° C.;

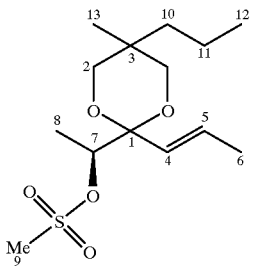

$^{1}$H-NMR (CDCl$_{3}$, 200 MHz): δ=5.9 (dq, 1H; H-5), 5.2 (d, 1H, H-4), 4.55 (q, 1H, H-7), 3.7–3.3 (m, 4H, H-2), 3.05 (s, 3H, H-9), 1.85 (d, 3H, H-6), 1.6 (m, 2H, H-10), 1.35 (d, 3H, H-8), 1.15/0.65 (s, 3H, H-13), 1.0 (q, 2H, H-11), 0.9 (t, 3H, H-12)

$^{13}$C-NMR (CDCl3, 50 MHz): δ=133.9 (C-5), 125.9 (C4), 98.8 (C-1), 83.1 (C-7), 69.8 (C-2), 28.7/36.6 (C-10), 38.4 (C-9), 32.9 (C-3), 19.6/19.0 (C-13), 17.8 (C-6), 16.7/15.7 (C-11), 15.9 (C-8), 14.9 (C-12)

| IR (Film): | ṽ [cm$^{-1}$] | vibration type |
| --- | --- | --- |
| | 3020, m | C—H stretching vibration, olefinic |
| | 2960, s | C—H stretching vibration, aliphatic |
| | 1670, w | C=C stretching vibration |
| | 1440, s + 1360, s | C—H deformation vibration |
| | 1415, m + 1175, s | sulfonate group |
| | 1110, s | C—O stretching vibration |

1.3.8 Reductive 1,2-rearrangement 4 g of the mesylate 57 (13 mmoles) were introduced under nitrogen into 40 ml of absolute toluene. The solution is cooled to −35° C., after which 30.5 ml of DI-BAH solution (1M in hexane) and 22.5 ml of triethyl aluminum solution (1 M in hexane) are added through a syringe. The solution is stirred for 2 h at −30° C., followed by careful quenching with 15 ml of saturated sodium hydrogen carbonate solution at a temperature of −20° C. After addition of 10 ml of distilled water, the precipitate is filtered off under suction and the filtrate is extracted with diethyl ether. After drying over sodium sulfate, the solvent is removed in a rotary evaporator and the residue is distilled in a bulb-tube oven. A clear colorless liquid is obtained.

Yield: 38%

Bp.: 90–100° C./0.1 mbar

Rotation angle: [α]$^{20}$$_{D}$=+6.28° (c=6.2);

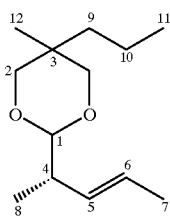

$^{1}$H-NMR (CDCl$_{3}$, 200 MHz): δ=5.5 (m, 2H; H-5/H-6), 4.25 (Ψ-t, 1H, H-1), 3.75 (d, 1H, H-2c$_{ax}$), 3.65 (d, 1H, H-2t$_{ax}$), 3.40 (d, 1 H, H-2t$_{eq}$), 3.35 (d, 1H, H-2c$_{eq}$), 2.35 (m, 1H, H-4), 1.7 (d, 3H, H-7), 1.55 (m, 2H, H-9), 1.25 (m, 2H, H-10), 1.15 (s, 1.5H, H-12t), 1.05 (d, 3H, H-8), 0.9 (m, 3H, H-11), 0.65 (s, 1.5H, H-12c);

$^{13}$C-NMR (CDCl$_{3}$, 50 MHz): δ=132.6 (C-6), 125.3 (C-5), 104.7 (C-1), 76.2/75.8 (C-2), 41.2 (C-4), 38.8/37.2 (C-10), 32.7 (C-3), 20.2/19.1 (C-12), 18.8 (C-7), 16.9/16.0 (C-10), 14.9 (C-11), 14.7 (C-8);

MS (70 eV): m/z (%)=212 (2) [M$^{+}$], 143 (60) [C$_{8}$H$_{15}$O$_{2}$$^{+}$], 97 (39 ) [C$_{6}$H$_{9}$O$^{+}$], 69 (22) [C$_{5}$H$_{9}$$^{+}$], 56 (18) [C$_{4}$H$_{8}$$^{+}$], 55 (100) [C$_{4}$H$_{7}$$^{+}$], 43 (16) [C$_{3}$H$_{7}$$^{+}$], 41 (29) [C$_{3}$H$_{5}$$^{+}$]

| IR (Film): | ṽ [cm$^{-1}$] | vibration type |
| --- | --- | --- |
| | 3020, w | C—H stretching vibration, olefinic |
| | 2960, s | C—H stretching vibration, aliphatic |
| | 1465, m + 1385, m | C—H-deformation vibration |
| | 1115, s | C—O stretching vibration |

1.3.9 Synthesis of optically active (−)-22

4.0 g of 5-methyl-2-(1-methyl-2-butenyl)-5-propyl-1,3-dioxane 58 (19 mmoles) are dissolved in 80 ml of cyclohexane and, after addition of 0.4 g of hydrogenation catalyst (5% palladium on carbon), the resulting solution is transferred to a steel autoclave. The mixture is stirred for 7 h under a pressure of 10 bar hydrogen and at a temperature of 80° C. After the catalyst has been filtered off and the solvent distilled off, the residue is distilled in a bulb-tube oven. A clear colorless liquid is obtained.

Yield: 81%

Bp.: 75–90° C./0.1 mbar

Rotation angle: [α]$^{20}$$_{D}$=−2.43° (c=5.2)

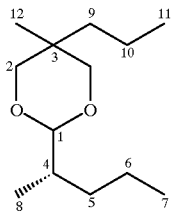

$^{1}$H-NMR (CDCl$_{3}$, 200 MHz): δ=4.25 (Ψ-t, 1H; H-1), 3.75 (d, 1H, H-2c$_{ax}$), 3.60 (d, 1H, H-2t$_{ax}$), 3.40 (d, 1H, H-2t$_{eq}$), 3.35 (d, 1H, H-2c$_{eq}$), 1.75–1.1 (m, 9H, H-4/H-5/H-6/H-9/H-10), 1.15 (s, 1.5H, H-12t), 1.05–0.8 (m, 9H, H-7/H-8/H-11), 0.65 (s, 1.5H, H-12c);

$^{13}$C-NMR (CDCl$_{3}$, 50 MHz): δ=105.3 (C-1), 76.4175.8 (C-2), 38.6/33.6 (C-9), 36.9 (C4), 32.7 (C-3), 20.3 (C-6), 18.8/16.7 (C-12), 15.9 (C-10), 15.0 (C-11), 14.2 (C-7),13.9 (C-8).

What is claimed is:

1. A process for the production of optically active 5-methyl-2-(1-methylbutyl)-5-propyl-1,3-dioxane comprising the steps of:

(a) forming an N,N-disubstituted lactamide by reacting an enantiomeric lactic acid methyl ester with piperidine or pyrrolidine;

(b) forming a protected N,N-disubstituted lactamide by reacting the N,N-disubstituted lactamide with ethyl vinyl ether;

(c) forming a protected α,β-unsaturated ketone by reacting the protected N,N-disubstituted lactamide with 1-propenyl magnesium bromide;

(d) forming an unprotected α,β-unsaturated ketone by removing the protective group;

(e) forming an acetal by reacting the unprotected αβ-unsaturated ketone with a 1,3-diol;

(f) forming a mesylated acetal by reacting the acetal with methane sulfonic chloride;

(g) reductively rearranging the mesylated acetal by reaction with diisobutyl aluminum hydride and triethyl to form 5-methyl-2-(1-methylbutenyl)-5-propyl-1,3-dioxane; and (h) reacting the 5-methyl-2(1-methylbutenyl)-5-propyl-1,3-dioxane with hydrogen to form 5-methyl-2-(1-methylbutyl)-5-propyl-1,3-dioxane.

2. A perfume composition consisting essentially of the product of the process of claim 1.

* * * * *